(12) United States Patent
Choo

(10) Patent No.: US 11,517,472 B2
(45) Date of Patent: Dec. 6, 2022

(54) VAGINAL BARRIER DEVICE APPARATUS AND METHOD

(71) Applicant: Kukhee Choo, New Orleans, LA (US)

(72) Inventor: Kukhee Choo, New Orleans, LA (US)

( * ) Notice: Subject to any disclaimer, the term of this patent is extended or adjusted under 35 U.S.C. 154(b) by 279 days.

(21) Appl. No.: 15/970,218

(22) Filed: May 3, 2018

(65) Prior Publication Data
US 2019/0336324 A1 Nov. 7, 2019

(51) Int. Cl.
*A61F 6/00* (2006.01)
*A61F 6/12* (2006.01)
*A61F 2/00* (2006.01)
*A61K 9/00* (2006.01)

(52) U.S. Cl.
CPC .............. *A61F 6/12* (2013.01); *A61F 2/0022* (2013.01); *A61K 9/0036* (2013.01)

(58) Field of Classification Search
CPC ...... A61F 6/06; A61F 6/08; A61F 6/14; A61F 6/146; A61F 6/148; A61F 2/005; A61F 2/0036; A61F 2/0004; A61F 2/0009; A61F 5/455; A61F 5/4553; A61F 13/20; A61F 13/2051; A61F 13/2022
USPC .......................... 128/834, 835, 833, 841, 839
See application file for complete search history.

(56) References Cited

U.S. PATENT DOCUMENTS

| | | | | |
|---|---|---|---|---|
| 1,891,761 A | * | 12/1932 | Goodard | A61F 5/4553 604/330 |
| 3,128,767 A | * | 4/1964 | Nolan | A61F 6/08 604/330 |
| 3,130,721 A | * | 4/1964 | Young | A61F 6/08 128/837 |
| 3,404,682 A | * | 10/1968 | Waldron | A61F 13/266 604/330 |
| 3,840,005 A | * | 10/1974 | Walker | A61F 6/144 128/839 |
| 3,841,333 A | * | 10/1974 | Zalucki | A61F 5/4553 604/330 |
| D239,416 S | | 3/1976 | Visor | |
| 5,417,226 A | * | 5/1995 | Juma | A61F 2/0009 128/885 |
| 5,513,659 A | * | 5/1996 | Buuck | A61F 2/0009 128/885 |
| 6,152,137 A | | 11/2000 | Schwartz et al. | |
| 6,832,983 B2 | | 12/2004 | Goodman | |
| D521,637 S | | 5/2006 | Yang | |
| D539,415 S | | 3/2007 | Fleming | |
| D745,135 S | | 12/2015 | Butler | |
| 2010/0204666 A1 | * | 8/2010 | Feloney | A61M 25/01 604/347 |
| 2010/0292665 A1 | | 11/2010 | Sigel et al. | |

(Continued)

FOREIGN PATENT DOCUMENTS

CN 101214093 A 7/2008
CN 201230592 5/2009

(Continued)

*Primary Examiner* — Adam Baker
(74) *Attorney, Agent, or Firm* — Miller IP Law

(57) ABSTRACT

A vaginal barrier device system and method for preventing entry of potentially contaminated fluid during immersion activities such as swimming or bathing, providing a secure fit, easy insertion and extraction, convenient cleaning, carrying, and storage, and avoiding irritation of the cervix or vaginal wall.

20 Claims, 10 Drawing Sheets

(56) References Cited

U.S. PATENT DOCUMENTS

2013/0123716 A1* 5/2013 Abbott .................. A61M 31/00
  604/285
2014/0083433 A1* 3/2014 Lowry ...................... A61F 6/08
  128/836
2015/0190305 A1* 7/2015 Maurette .................. A61F 6/08
  128/830

FOREIGN PATENT DOCUMENTS

| HU | 200302218 A1 | | 6/2005 |
| WO | WO 2008/058545 | * | 5/2008 |
| WO | WO2008058545 A1 | | 5/2008 |

* cited by examiner

VAGINAL BARRIER DEVICE APPARATUS AND METHOD

BACKGROUND

This invention provides a vaginal barrier device apparatus and method for preventing entry of potentially contaminated fluid during immersion activities such as swimming or bathing.

When a woman immerses herself up to her pelvis in a fluid, such as fresh water or saltwater, but also including other fluids such as muds, mineral waters, and the like, in activities such as swimming or bathing, but also including other activities subjecting a woman to immersion or a very heavy or forceful spray of a fluid, there is a tendency for fluid to enter the vagina. Such fluid might itself be irritating to the vaginal wall and cervix, and such fluid might be contaminated with debris or substances that are irritating or otherwise unsafe and unhealthy. There are locales around the world where clean water is scarce, and rising global temperatures tend to increase bacterial, fungal, and parasitical proliferation in open waters such as ponds, rivers, lakes, seas, and even swimming pools. Swimming pools heavily utilize sanitation products, such as chlorine, to keep the water from overpopulating in bacteria, fungi, and so forth. Municipal water sources also add chemicals such as fluoride. Some women have been reported to be sensitive to certain chemicals in waters. Activities in contaminated or chemically altered waters may put women's reproductive and general health at risk.

There is a need for a device and method to help protect against vaginal infiltration of fluids such as water when engaging in activities that require such immersion.

Existing devices and methods tend to be cumbersome, inconvenient, and irritating, especially with devices that make contact with the cervix. Such existing devices also tend to be difficult to keep clean and sterile.

For example, Chinese Patent Application Publication No. 101214093 A, as published on Jul. 9, 2008, covers a protection tool for female swimming. Specifically, the tool has an elastic rubber head utilized for closing vaginal orifice. The height of the elastic rubber head is about 2 to 5 centimeter, length of the head is about 1.5 to 5 centimeter, and the width of the head is about 1.5 to 5 centimeter. An upper part of the elastic rubber head has convex arc shaped surface. A protruding support ring is formed around lower part of the convex arc shaped surface in the middle of the elastic rubber head. The bottom of the elastic rubber head is fixed on a soft rubber cushion capable of approximately covering female vulva.

Hungarian Patent Application Publication No. 200302218 A1, as published on Jun. 28, 2005, covers a hygienic device for women who may be immersed in water. Here, a hygienic device is proposed for women, to ensure secure bathing in rivers, lakes, swimming pools, etc. The device is intended to stop water and polluting debris entering the vagina. Its lower end is a tight fit, closing the entrance to the vagina. Its upper end, which is enlarged, and supported by the strong muscles of the central part of the vagina.

Chinese Patent Application Publication No. 201230592 Y, as published on May 6, 2009, covers a healthcare sex protector for use during swimming by a woman. Specifically, the protector has an oval-shaped plunger part made from silica gel or rubber materials and placed in a female vaginal orifice, where the plunger part is connected with a shielding part. The shielding part shields a female vulva, and an inside part of the shielding part is equipped with a clamp spring. A place between the plunger part and the shielding part is installed with a connecting piece. The plunger part includes a clamping opening, and an end of the connecting piece is connected with the shielding part.

International Publication No. WO 2008/058545 A1 was published on May 22, 2008, disclosing a "Vaginal Protection Device." The invention concerns a vaginal protection device comprising at least one central anchoring part and two or more protruding and circumferential at least partly flexible sealing elements with a larger outer circumference than the anchoring part, such that the sealing elements at least partly lie against the vagina walls, when the protection device is inserted into the vagina. In one embodiment, the protection device may be inflatable. Further, this invention concerns the application of such a vaginal protection device for abdominal protection, as contraceptives and for sampling from the vagina and the vagina walls.

U.S. Pat. No. 6,832,983 entitled "Article of Clothing with a Novel Attachment Means," issued on Dec. 21, 2004 to inventor John Mott Goodman. Here, provided is an article of clothing including extensions for insertion into a body cavity, thereby permitting swimsuits, undergarments, and several other types of clothing to be secured in place with a minimum of fabric. The articles are made dimensionally stable to maintain their position and orientation relative to the wearer's body. More relevant, described is a vaginal-insert extension, and its means of attachment to the design of frame. This extension is formed as a hollow resilient bulb of soft rubber or plastic, with a skirt at the bottom end. The surface of the extension is soft, smooth, and washable to avoid any possibility of damage to the sensitive surfaces inside the vagina. These properties render it unlikely to retain harmful microorganisms and makes cleaning it very easy. When the extension is in place, the lower portion of the bulbous part bears on the inside of the muscular ring surrounding the vaginal opening, thus keeping the suit in close contact with the wearer's body. The bulb's skirt flares out over the frame-attachment mechanism and protects the wearer from contact with that hard surface, plus it protects the suit from possible fluid leakage from the vagina. Also provided is a variation of the above-described vaginal-insert extension, whereby the top of the bulb is removed entirely. Thus, this extension has a trumpet-like shape, which can be folded for insertion or removal, and which—while in the vagina—will flare out and bear on the inner surface of the ring of muscles surrounding the vaginal opening. Moreover, provided is another variation of the above-described vaginal-insert extension, whereby it is hollow and is provided with a reclosable opening. Further, there is a valve located on the underside of the extension's skirt, which valve can be operated by the wearer through the fabric covering of the suit. This valve permits one to expel the air inside the bulb to facilitate insertion of it, and then—after the bulb has expanded inside the wearer's body—to seal the bulb, so water cannot leak inside during swimming, for example. When it is time to remove the extension, the wearer can easily open the valve, once again permitting the bulb to be compressed easily during its withdrawal.

U.S. Design Pat. No. D745,135 was issued on Dec. 8, 2015 to assignee Bumble BE Holdings, LLC for an "Earplug." The '135 Design patent covers an ornamental design for an earplug.

U.S. Design Pat. No. D239,416 was issued on Mar. 30, 1976 to assignee Flents Products Co., Inc. for an "Ear Plug or the Like," and covers the ornamental design for an earplug or the like.

U.S. Design Pat. No. D539,415 was issued to assignee Howard Leight Industries, Inc. on Mar. 27, 2007 for a "Flange Earplug," particularly covering the ornamental design for a flange earplug.

U.S. Design Pat. No. D521,637 was issued on May 23, 2006 to assignee All-Logic Int. Co., Ltd. for an "Ear Plug," and covers the ornamental design for an earplug.

U.S. Pat. No. 6,152,137 for a "Pliable and Resilient Sealing Pad," as issued on Nov. 28, 2000, provides for a pliable and resilient sealing pad for isolation of the user's skin from the outside environment and a method for attaching a gelatinous elastomer which may be used in such pad, conceptualized by inventors Alan N. Schwartz and Thomas D. Theisen. More specifically, the sealing pad is made of a compliant and resiliently deformable gelatinous elastomer suitable to conform under pressure to form a substantially airtight seal with at least a portion of the user's skin adjacent to the sealing pad. The gelatinous elastomer may be attached to a second material by incorporating the gelatinous elastomer into a large plurality of interstitium in the second material. In addition, the second material can be configured to form an endoskeleton or exoskeleton that modifies the physical properties of the gelatinous elastomer. More relevant, in a particular embodiment, the sealing pad can partially isolate a human orifice, such as the mouth, the nose, the ears, the eyes, the urethra, the vagina, or the rectum. The sealing pad can be used to isolate, partition, or alter the direction of flow of bodily fluids and gases that include but are not restricted to tears, blood, cerebrospinal fluid, semen, vaginal fluids, mucous, sweat, breath, urine and fecal material. An example of this embodiment is a sealing pad that can form a watertight seal between a pair of infant or toddler diapers and the outside environment, thereby preventing leakage.

Lastly, U.S. Patent Application Publication No. 2010/0292665 A1 was published on Nov. 18, 2010, disclosing a "Sanitary Waterproof Pad for Tweens." Inventors Susan Sigel and Sari Kleinman conceptualized a sanitary pad for tween girls for use under a swimsuit. The sanitary pad includes a body having a size and shape conforming to a genital area of an average tween girl and is inconspicuous while being worn by the tween under her swimsuit. The body has a waterproof outer layer, an inner lining and a peripheral edge. The waterproof outer layer has a removable backing covering an adhesive such that upon removal of the backing, the body is removably adherably positionable in the swimsuit and remains in place during vigorous swimming activities and play, whether in or out of the water. The inner lining is capable of absorbing menstrual fluid. A vaginal plug is positioned on the inner lining so as to align comfortably at the opening of the tween's vagina.

What is needed is a device and method that is easy, convenient, non-irritating, and easy to clean and keep sterile.

SUMMARY OF THE INVENTION

This invention provides a vaginal barrier device system and method for preventing entry of potentially contaminated fluid during immersion activities such as swimming or bathing, providing a secure fit, easy insertion and extraction, convenient cleaning, carrying, and storage, and avoiding irritation of the cervix or vaginal wall.

BRIEF DESCRIPTION OF DRAWINGS

Reference will now be made to the drawings, wherein like parts are designated by like numerals, and wherein.

DETAILED DESCRIPTION OF THE INVENTION

Figure 1:
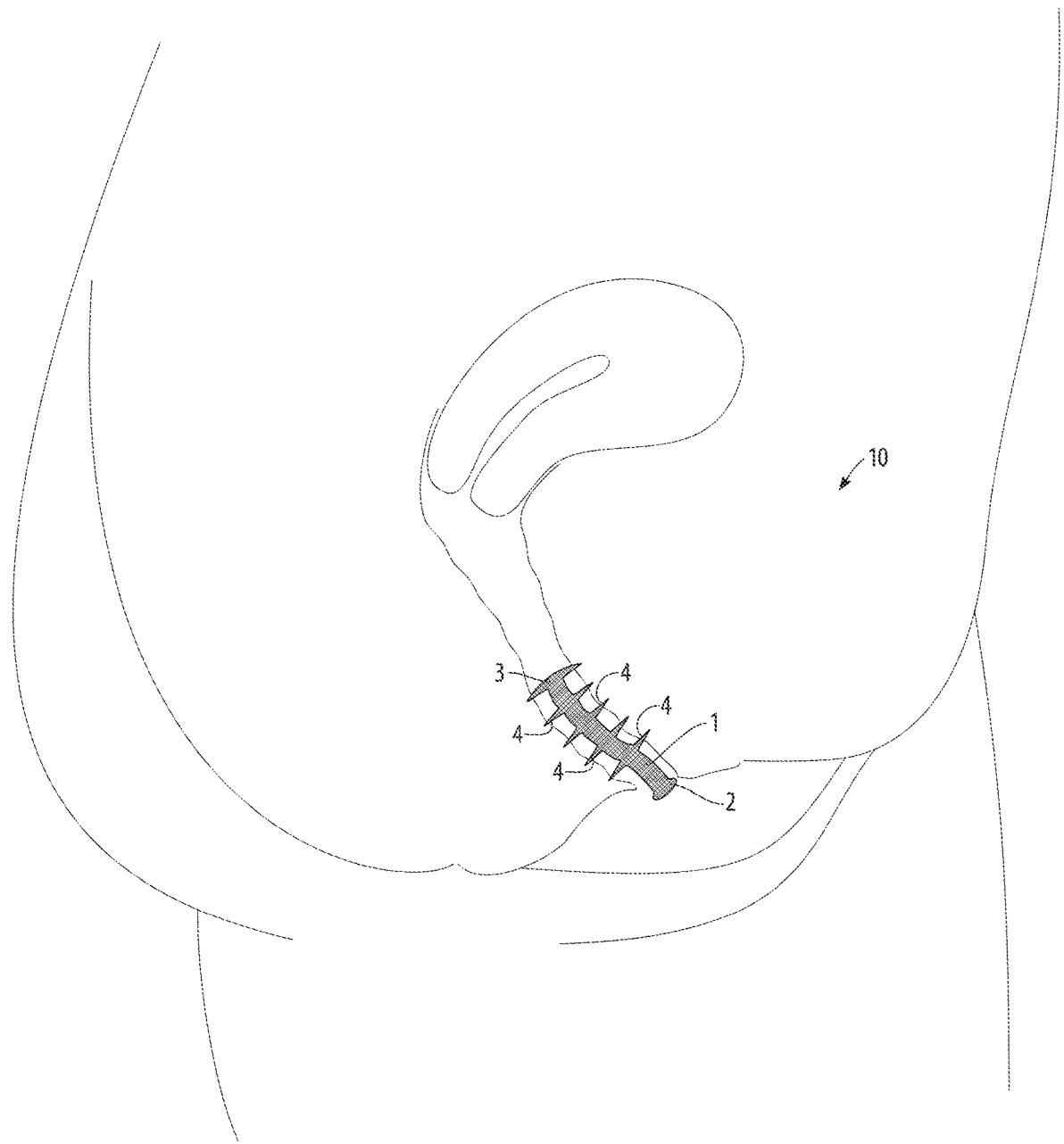
FIG. 1 is a schematic view of the vaginal barrier device of the invention in use.

Referring to FIG. 1, the vaginal barrier device 10 of the invention is shown schematically in use by a human female. The vaginal barrier device 10 provides a flexible stem 1, an end grip 2, a domed first circular barrier 3, and at least three intermediate circular barriers 4. The circular barriers are substantially co-axial with the stem and are of one continuous piece with the stem with no seams and no separate or separable pieces. In use, after insertion and prior to extraction, the circular barriers extend substantially perpendicular to the relevant part of the flexible stem 1, each with its circumference pressed gently to the vaginal wall and conforming to the vaginal wall, providing independent points of sealing.

The vaginal barrier device 10 is formed as a single piece without joints, creases, or crevasses likely to trap substances and make the device difficult to clean and keep sterile between uses. The vaginal barrier device 10 is meant to be very easy to clean, even by boiling or autoclaving, if desired.

The vaginal barrier device 10 is made of a material having the properties of being able to deform under slight pressure but being stiff enough to return to original shape in the absence of such pressure. A silicone rubber material with a Shore hardness in the range of 2A to 25A is appropriate. The material should be "skin safe", conforming to a standard such as ISO 10993-10 or OECD TG 439, and should not leech out any substance or absorb any substance after curing, in use. The material should withstand high heat and harsh chemicals which might be used for cleaning and sterilization between uses. The material should allow casting in a mold in one piece. Such silicone rubbers are known and are available for use in manufacturing the vaginal barrier device 10.

Figure 2:
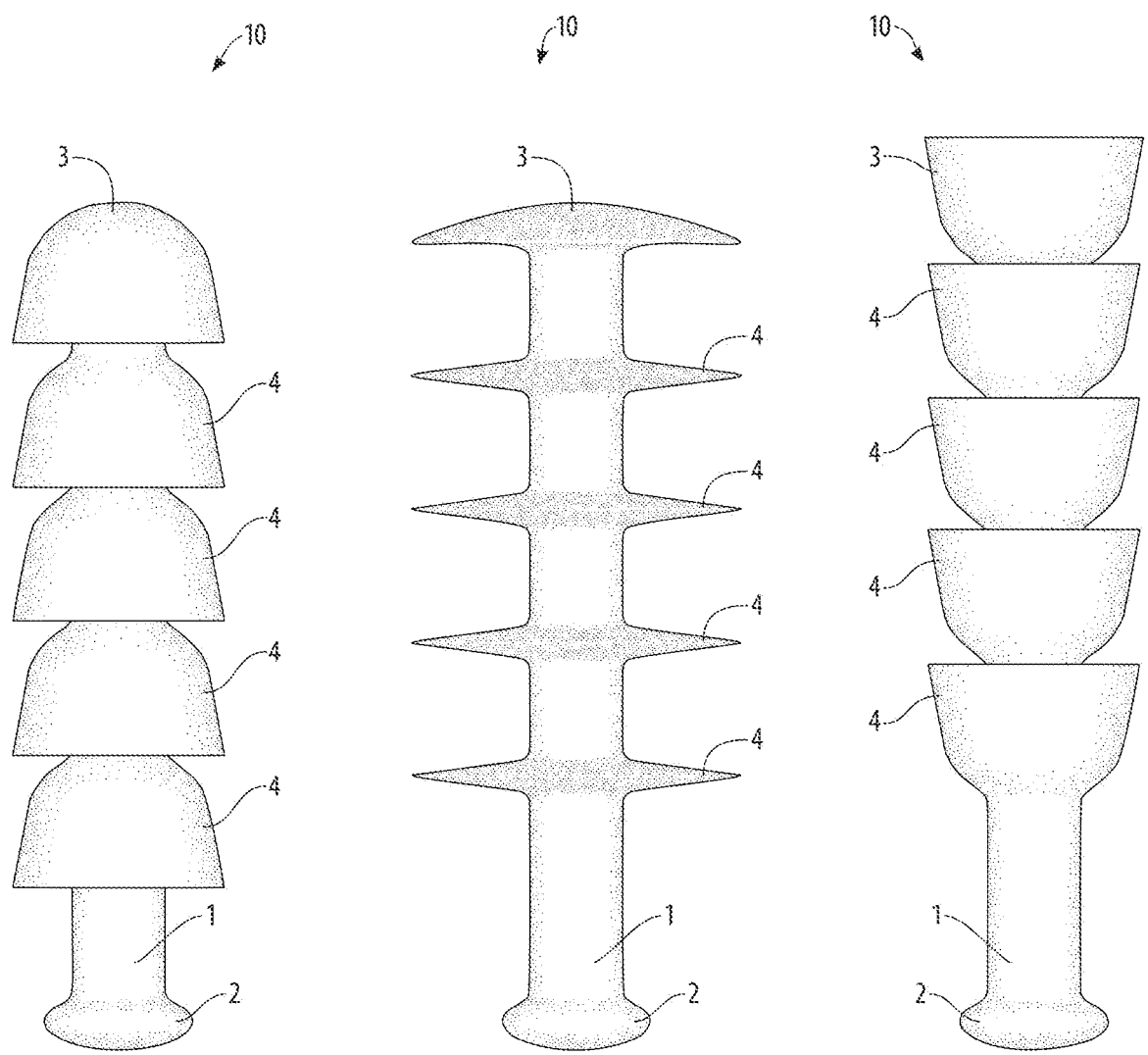
FIG. 2 is a side view of an embodiment of the vaginal barrier device of the invention in three states of use.
Figure 3:
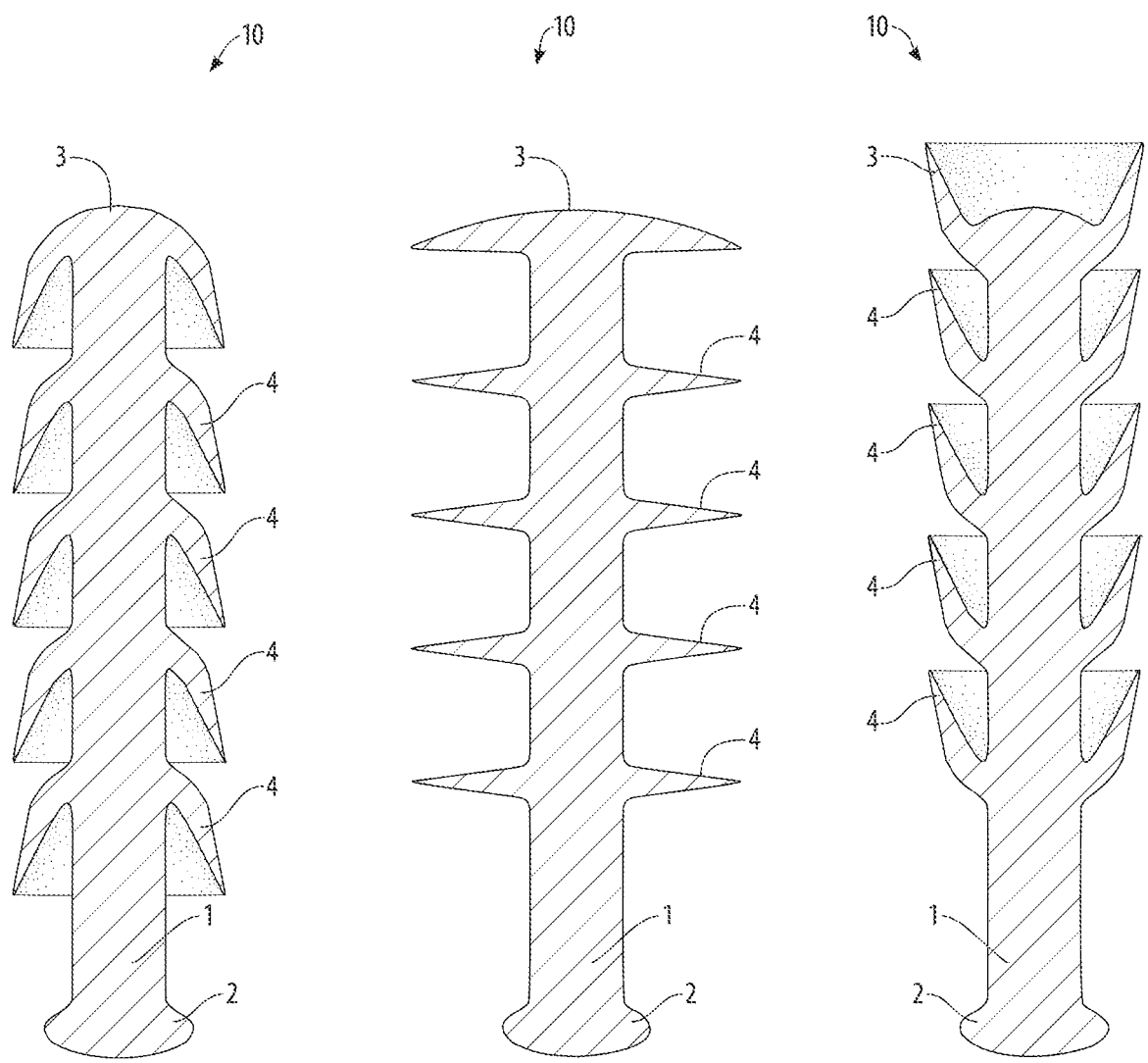
FIG. 3 is a cross-section view of an embodiment of the vaginal barrier device of the invention in three states of use.

Referring to FIG. 2 and FIG. 3, the vaginal barrier device 10 is manufactured as a single unit of flexible material, so the flexibility of any particular part of the vaginal barrier device 10 is controlled by the relative thickness or thinness of the part. The flexible stem 1 is relatively thick, and is relatively more resistant to deformation or bending, which is appropriate because only slight bending is needed in use. The domed first circular barrier 3 and the intermediate circular barriers 4 taper down from relative thickness close to the flexible stem 1 to relative thinness at the circumference of each. The thick portion provides a force tending to restore the circular barrier to its full-out resting position, while the thinner circumferential portion more readily conforms to the vaginal wall, efficiently sealing but not applying a discomfort-causing excess of pressure.

The domed first circular barrier 3 and the intermediate circular barriers 4 are capable of deforming upwards and downwards, which causes the diameter of the circle to be smaller for the purposes of insertion and extraction. The flexible stem 1 is provided with an end grip 2 to allow easier manipulation of the vaginal barrier device 10. The end grip 2 should provide enough surface variation to facilitate manipulation, but not so much or so sharp-edged as to cause discomfort in use, with the end grip 2 resting in, or close to, the vaginal entrance. The end grip 2 can be implemented as an outward bulge, as illustrated, or as one or more grooves or ridges at the end of the flexible stem 1.

The size of the vaginal barrier device 10 is appropriate to its use, and should not make contact with the cervix in normal use. Contact with the cervix is not needed for the functioning of the vaginal barrier device 10, and such contact would likely be irritating to the cervix. However, if such contact is made, the domed first circular barrier 3 is configured to provide a minimally irritating contact surface. A preferred embodiment of the vaginal barrier device 10 has dimensions in the ranges of 6 cm to 7 cm in length of the flexible stem, 0.5 cm to 1 cm in diameter of the flexible stem, 2 cm to 3 cm in diameter of the domed first circular barrier and the three or four intermediate circular barriers, 0.5 cm to 1 cm increments of spacing between the circular barriers, and 2 mm to 3 mm in thickness of the circular barriers at the stem, tapering down towards the circumference.

Figure 4:
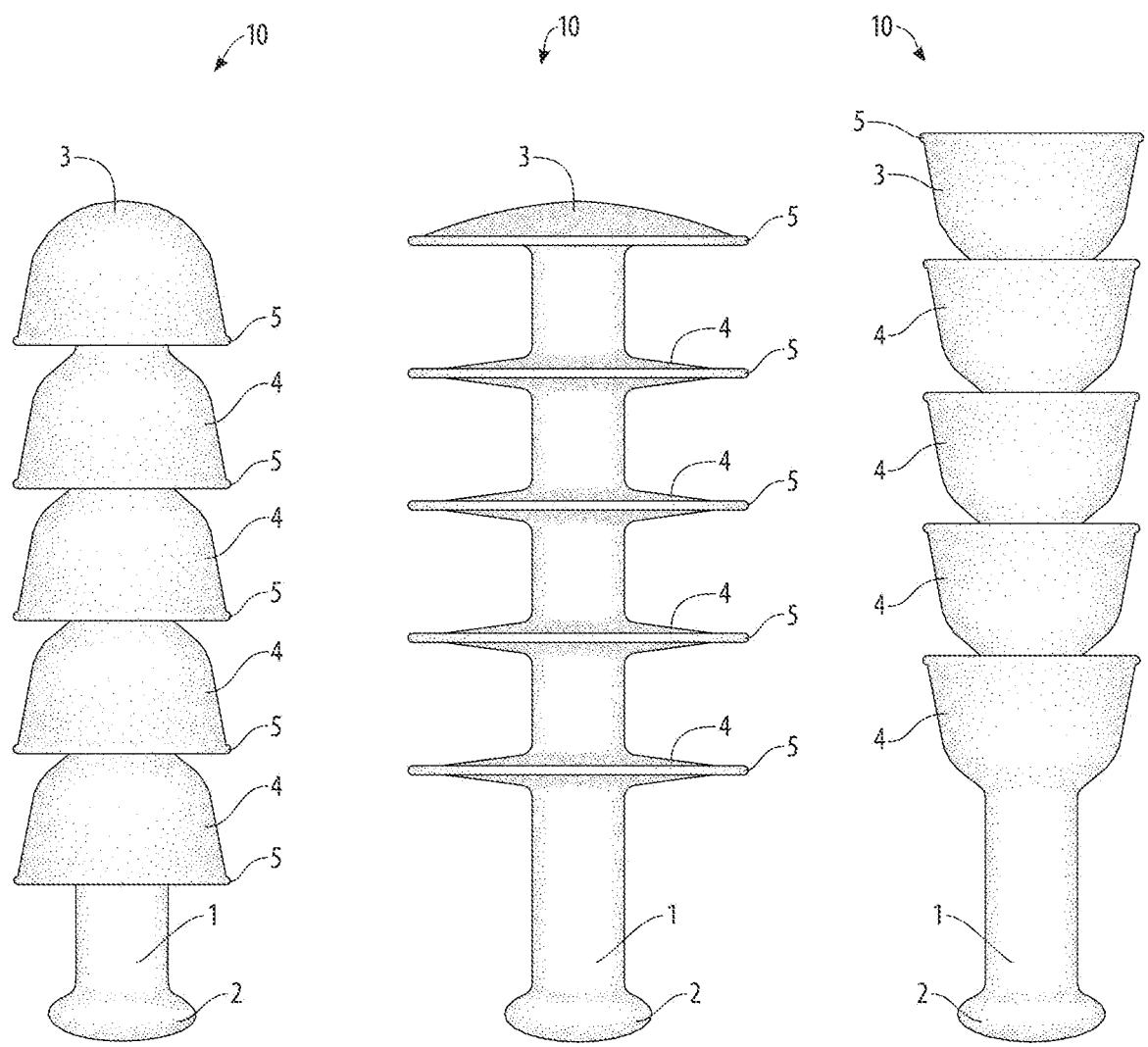
FIG. 4 is a side view of another embodiment of the vaginal barrier device of the invention in three states of use.
Figure 5:
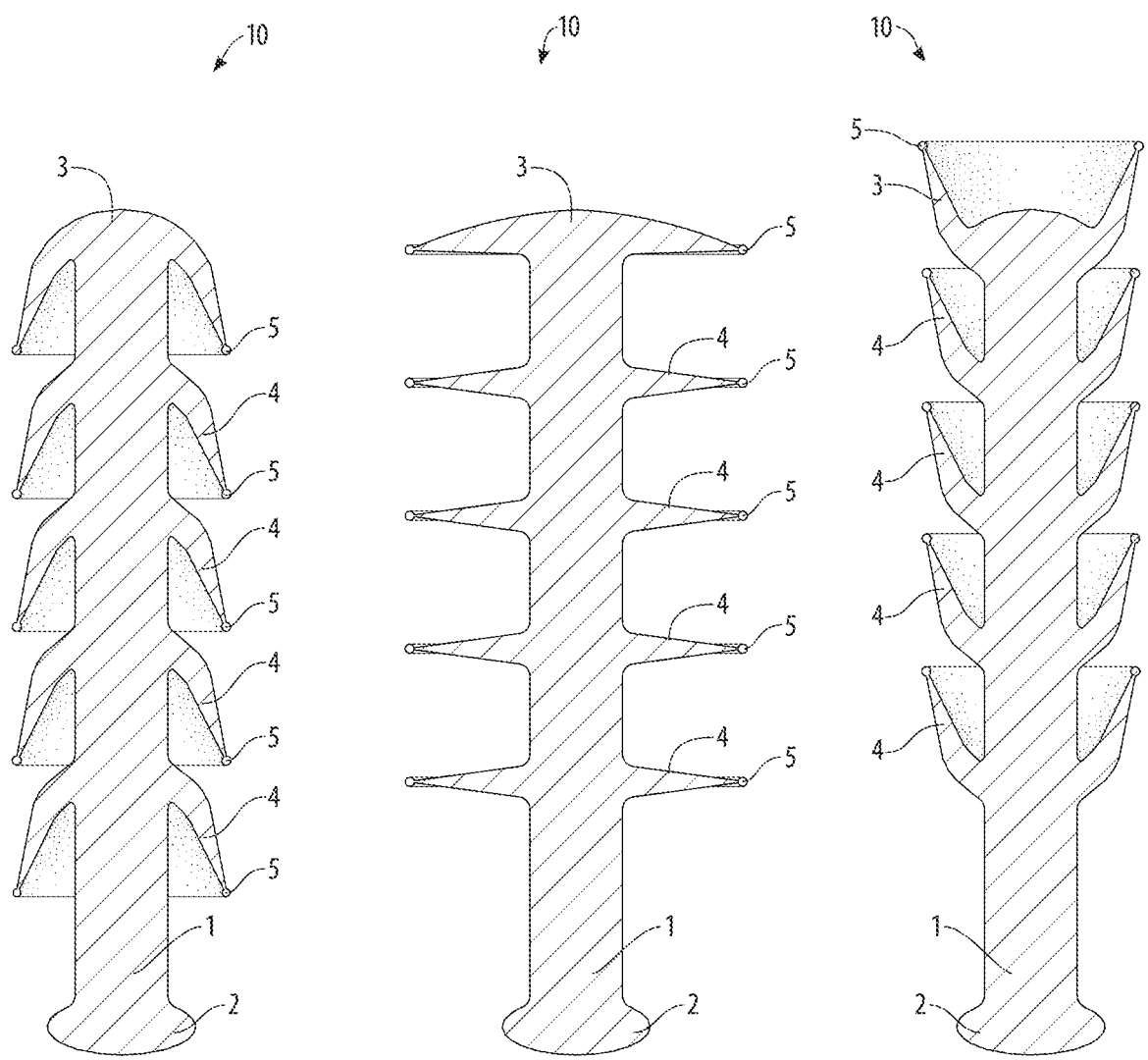
FIG. 5 is a cross-section view of another embodiment of the vaginal barrier device of the invention in three states of use.

Referring to FIG. 4 and FIG. 5, another embodiment of the vaginal barrier device 10 further provides a beaded circumference 5 of the domed first circular barrier 3 and intermediate circular barriers 4. This additional thickness of material at the circumference increases the tendency of the circumference to return to shape after deformation, exerting somewhat more pressure on the vaginal wall, but providing a somewhat improved seal. When designing such a beaded circumference 5, care should be taken to avoid forming a crease or crevice which can trap substances and make the device difficult to clean and keep sterile.

Figure 6:
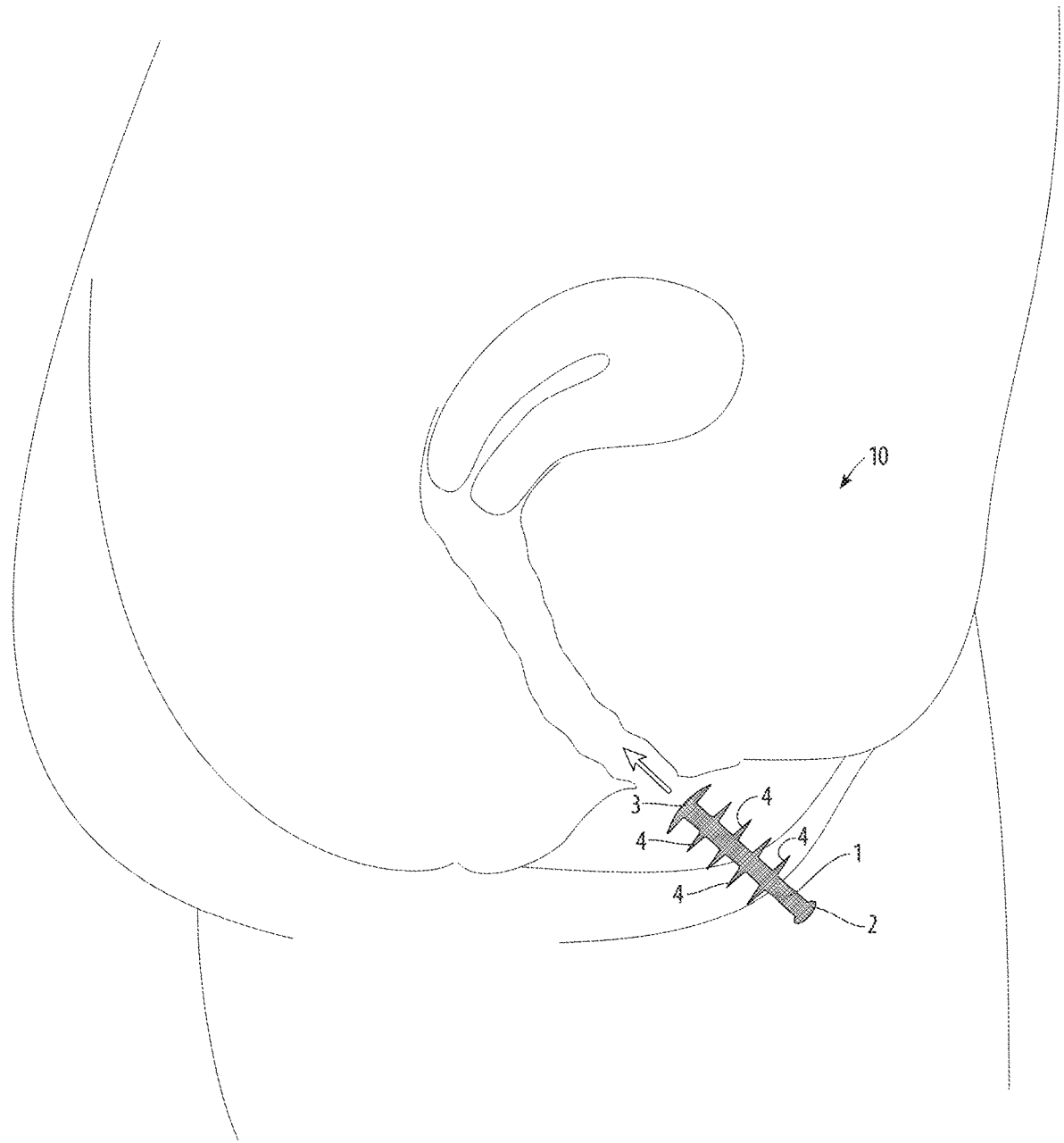
FIG. 6 is a schematic view of the vaginal barrier device of the invention in a prior-to-insertion state of use.

Referring to FIG. 6, in use, prior to insertion, the vaginal barrier device 10, is in its resting configuration, with the domed first circular barrier 3 and the intermediate circular barriers 4 extended outward.

Figure 7:
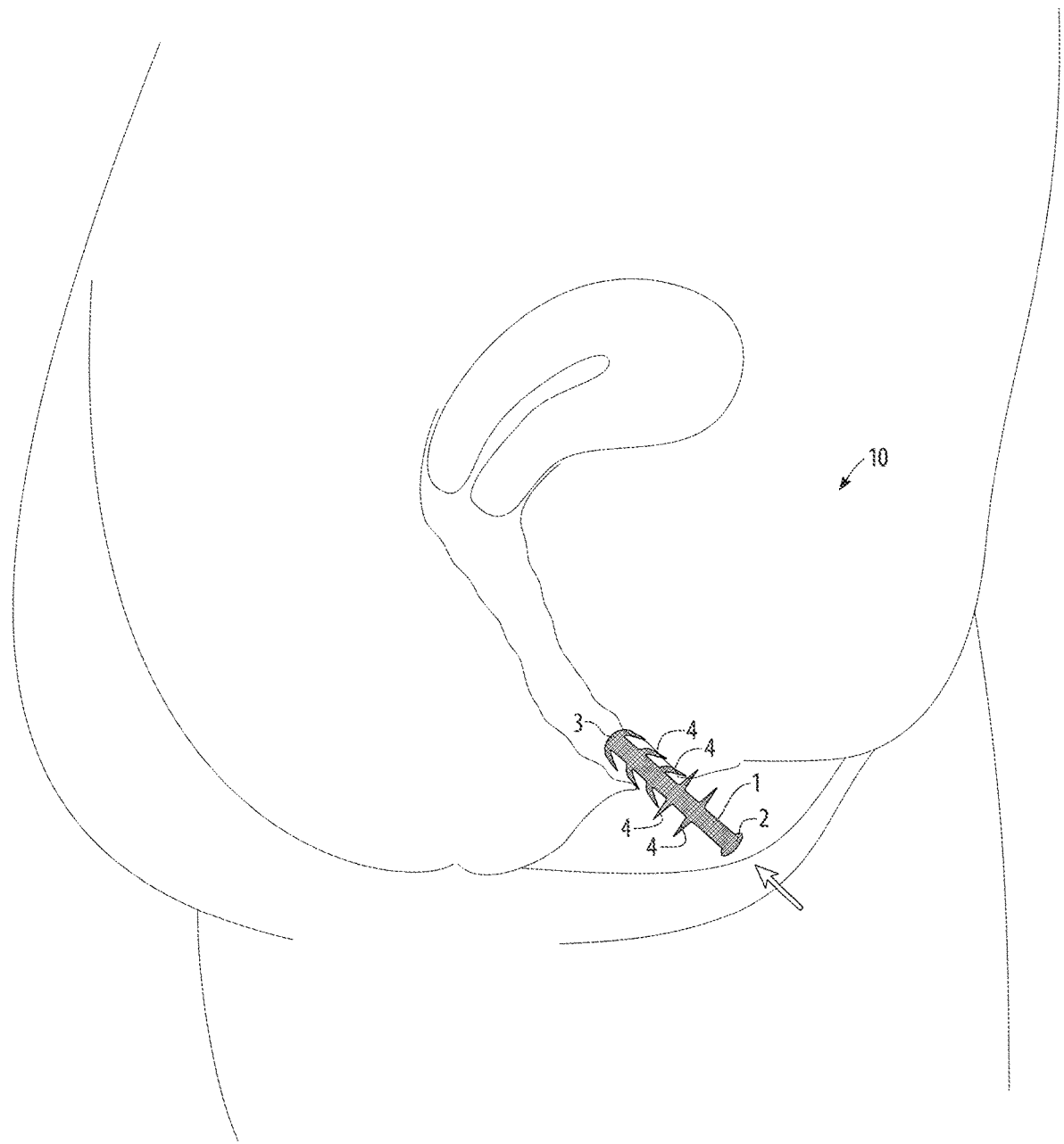
FIG. 7 is a schematic view of the vaginal barrier device of the invention in a partial-insertion state of use.
Figure 8:
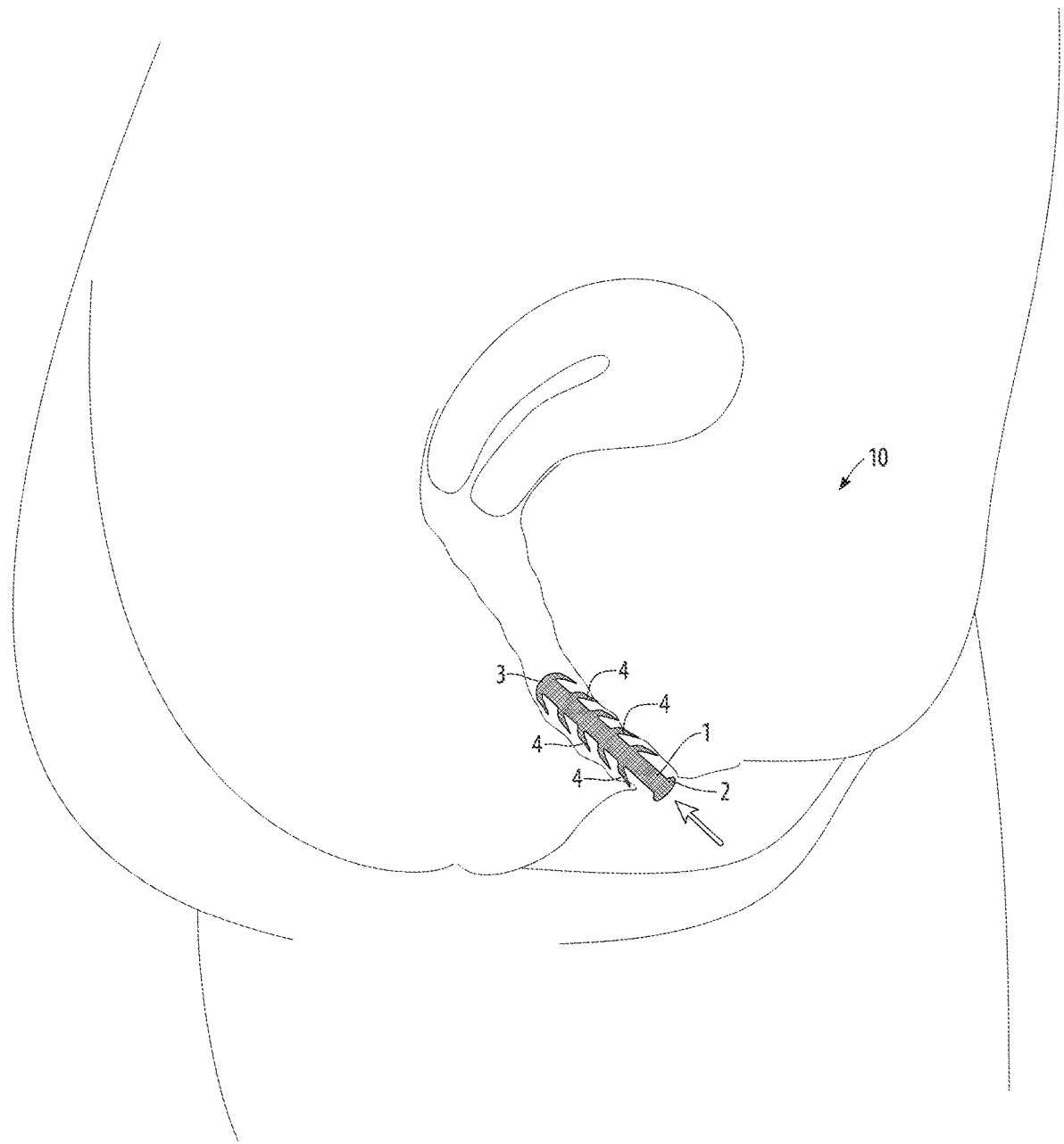
FIG. 8 is a schematic view of the vaginal barrier device of the invention in a full-insertion state of use.

Referring to FIG. 7 and FIG. 8, in use, during insertion of the vaginal barrier device 10, the domed first circular barrier 3 and the intermediate circular barriers 4 deform downwards, causing the diameters to be smaller, and facilitating insertion.

Figure 9:
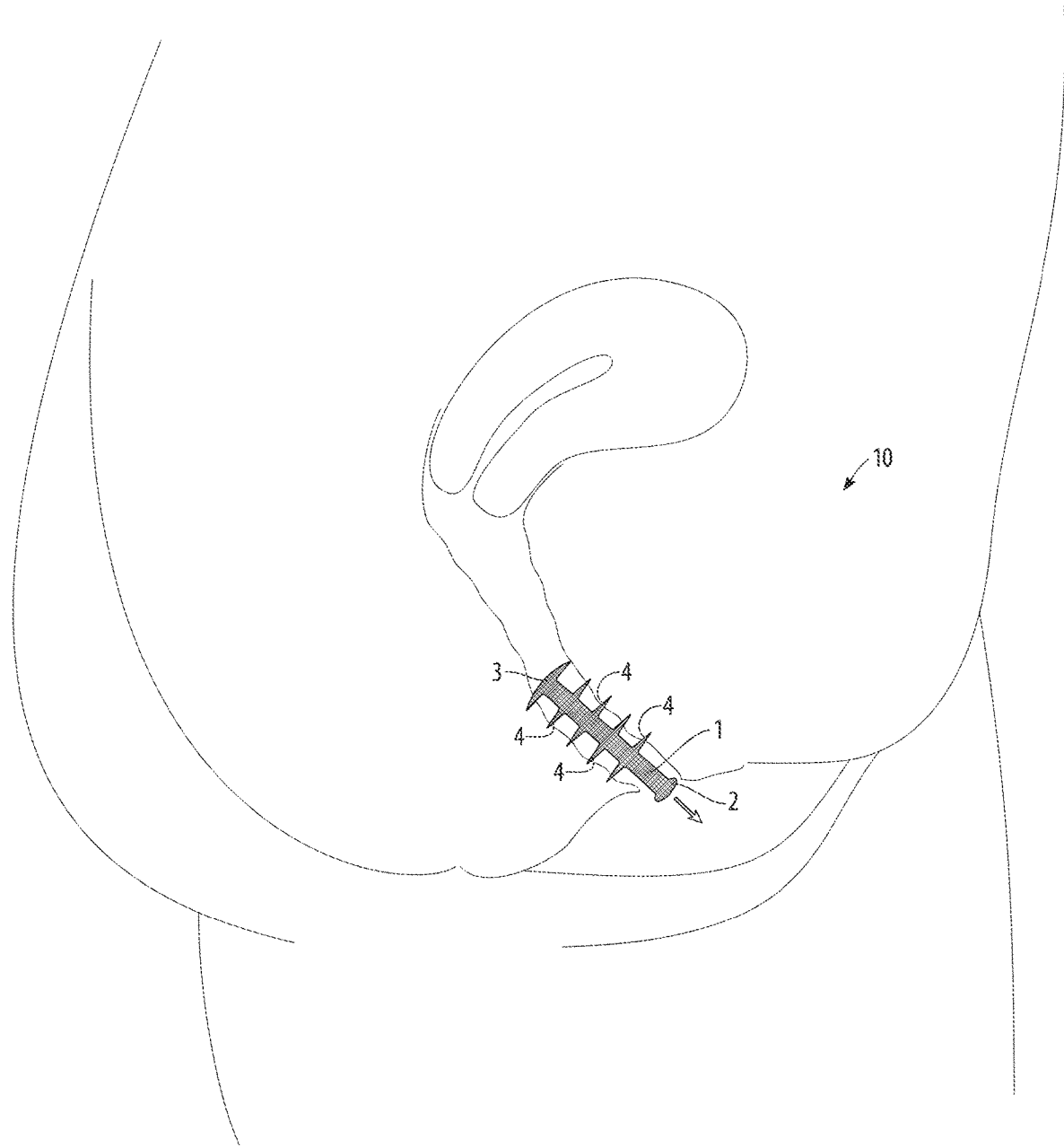
FIG. 9 is a schematic view of the vaginal barrier device of the invention in a set state of use.

Referring to FIG. 9, in use, after insertion, the vaginal barrier device 10 is pulled slightly outward, using the end grip 2, thereby setting the domed first circular barrier 3 and intermediate circular barriers 4 into an extended state, forming seals by exerting slight pressure against the vaginal wall.

Figure 10:
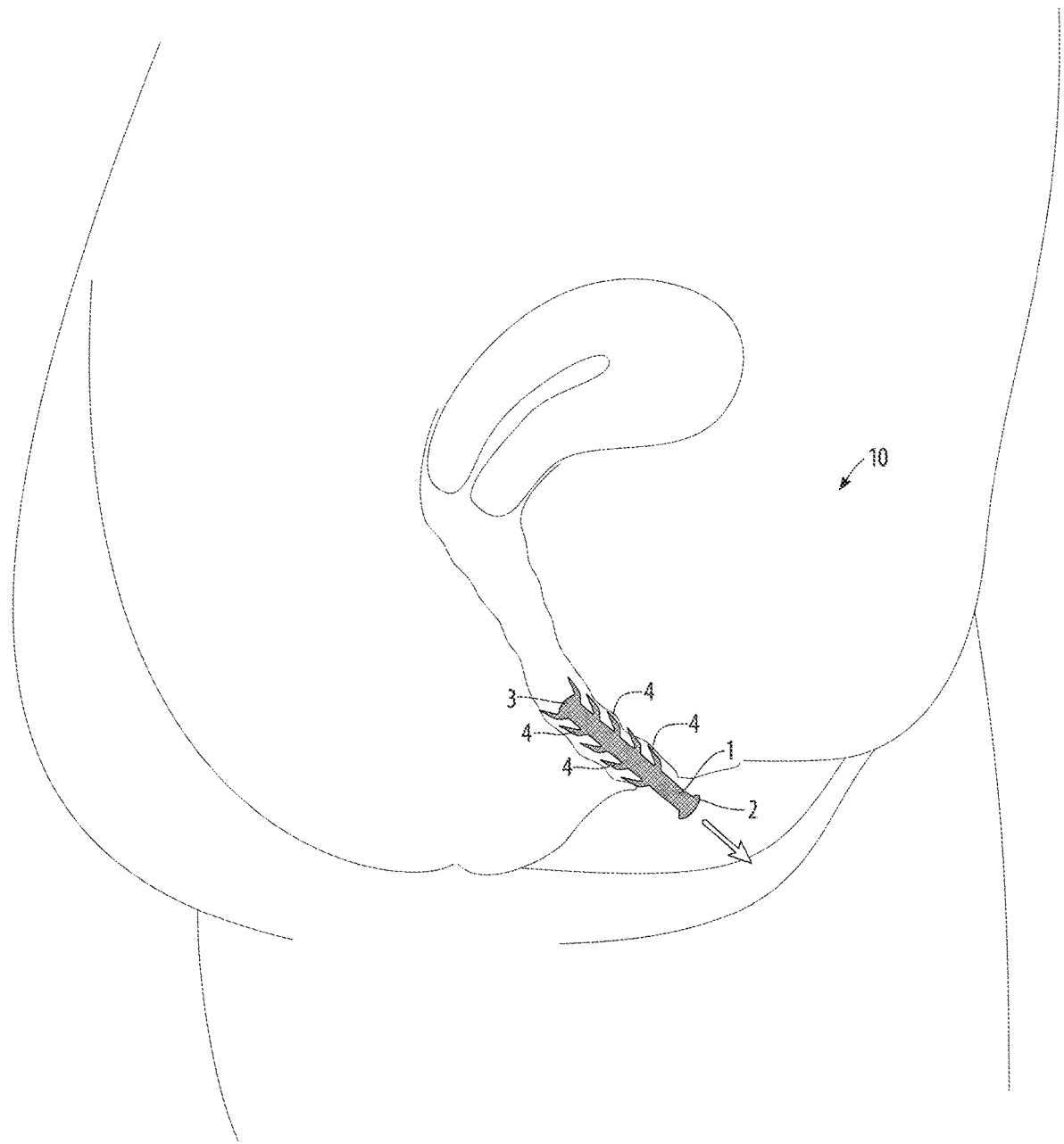
FIG. 10 is a schematic view of the vaginal barrier device of the invention in an extraction state of use.

Referring to FIG. 10, in use, the vaginal barrier device 10 is extracted by an outward pulling, using the end grip 2, causing the domed first circular barrier 3 and intermediate circular barriers 4 to deform upwards, causing the diameters to be smaller, and facilitating extraction.

Many other changes and modifications can be made in the system and method of the present invention without departing from the spirit thereof. I therefore pray that my rights to the present invention be limited only by the scope of the appended claims.

I claim:

1. A vaginal barrier device apparatus for preventing entry of potentially contaminated fluid during immersion activities, the vaginal barrier device comprising:
   a unitary flexible body configured for positioning in a vaginal opening, the flexible body having:
      a flexible stem of substantially uniform linear and non-hollow cylindrical form, having a long axis between an upward end and a downward end and a substantially uniform cross-sectional geometry along a length of the flexible stem, said body being configured to seal off the vaginal opening to prevent an entry of fluid into a vaginal canal, while a portion of the stem extends into the vaginal canal;
      an end grip at the downward end of said flexible stem, said end grip resting at the vaginal opening when said vaginal barrier device is in use;
      a first circular barrier at the upward end of said flexible stem, said first circular barrier having an upwardly facing outwardly convex central portion and a bendable disk-shaped sealing portion unitary connected to, and extending outwardly from, the central portion; and
      at least three intermediate circular barriers arrayed in a spaced-apart relationship along said flexible stem;
   where said first circular barrier and each said intermediate circular barrier is arrayed co-axially upon said flexible stem, with ends extending, at rest, substantially perpendicularly radially from said flexible stem, the extended ends each defining a resting circumference co-axial with said flexible stem; where said first circular barrier and each said intermediate circular barrier have a tapering profile from a relative thickness portion at said flexible stem to a relative thinness portion near the circumference of each;
   where said sealing portion of the first circular barrier and each said intermediate circular barrier are adapted to flex downward upon insertion and flex upward upon extraction, each thereby defining a circumference smaller than the resting circumference when flexed; wherein, when the device is positioned, the thickness portions of the first circular barrier and each said intermediate circular barrier provides a force tending to restore the circular barrier to its resting position which urges the thinness portions of the first circular barrier and each said intermediate circular barrier against a vaginal wall to seal off the vaginal opening and prevent entry of fluids into the vaginal canal from an exterior of a woman's body; said vaginal barrier device is capable of being used to seal the vagina against intrusion of fluid from the exterior of the woman's body and prevent, entry of potentially contaminated fluid during immersion activities.

2. The vaginal barrier device of claim 1, said sealing portion of the outwardly convex first circular barrier and said intermediate circular barriers further comprising a rounded circumferential outer edge.

3. The vaginal barrier device of claim 1, said single unit of flexible material further comprising a silicone rubber material.

4. The vaginal barrier device of claim 1, said single unit of flexible material further comprising a silicone rubber material having a Shore hardness in the range of 2A to 25A.

5. The vaginal barrier device of claim 1, said single unit of flexible material further comprising a silicone rubber proven to be safe for prolonged contact with skin, in conformance with standards ISO 10993-10 and OECD TG 439.

6. The vaginal barrier device of claim 1, said single unit of flexible material further comprising a silicone rubber allowing casting in a mold in one piece.

7. The vaginal barrier device of claim 1, said single unit of flexible material further comprising a silicone rubber that does not leech out any substance or absorb any substance after curing, in use.

8. The vaginal barrier device of claim 1, said single unit of flexible material further comprising a silicone rubber capable of withstanding high heat and harsh chemicals used for cleaning and sterilization.

9. The vaginal barrier device of claim 1, further having dimensions appropriate to use within a human vagina without making contact with the cervix.

10. The vaginal barrier device of claim 1, further having dimensions in the ranges of 6 cm-7 cm in length of said flexible stem, 0.5 cm-1cm in diameter of said flexible stem, 2 cm-3 cm in diameter of said first circular barrier and said intermediate circular barriers, 0.5 cm-1cm increments of spacing between said circular barriers, and 2 mm-3 mm in thickness of said circular barriers at said flexible stem, tapering down towards the circumference.

11. A vaginal barrier device method, comprising:
providing a vaginal barrier device, further comprising:
a unitary flexible body having:
a flexible stem of substantially uniform linear and non-hollow cylindrical form, having a long axis between an upward end and a downward end and a substantially uniform cross-sectional geometry along a length of the flexible stem;
an end grip at the downward end of said flexible stem;
a first circular barrier at the upward end of said flexible stem, said first circular barrier having an outwardly convex central portion and a bendable disk-shaped sealing portion unitary connected to, and extending outwardly from, the central portion; and
at least three intermediate circular barriers arrayed in a spaced-apart relationship along said flexible stem;
where said first circular barrier and each said intermediate circular barrier is arrayed co-axially upon said flexible stem, extending, at rest, substantially perpendicularly radially from said flexible stem, the extended ends each defining a resting circumference co-axial with said flexible stem;
where said sealing portion of the first circular barrier and each said intermediate circular barrier have a tapering profile from relative thickness at said flexible stem to relative thinness near the circumference of each; and
where said first circular barrier and each said intermediate circular barrier are adapted to flex downward upon insertion and flex upward upon extraction, each thereby defining a circumference smaller than the resting circumference when flexed;
positioning said vaginal barrier device in a vaginal opening such that the outwardly convex central portion of the first circular barrier is oriented upwardly, while the sealing portion of the first circular barrier and each said intermediate circular barrier urge against a vaginal wall, while sealing off the vaginal opening and preventing entry of fluids into a vaginal canal from exterior of a woman's body; and
using said vaginal barrier device to seal the vagina against intrusion of fluid from exterior of the woman's body and prevent, entry of potentially contaminated fluid during immersion activities.

12. The vaginal barrier device method of claim 11, said sealing portion of the outwardly convex first circular barrier and said intermediate circular barriers further comprising a rounded circumferential outer edge.

13. The vaginal barrier device method of claim 11, said single unit of flexible material further comprising a silicone rubber material.

14. The vaginal barrier device method of claim 11, said single unit of flexible material further comprising a silicone rubber material having a Shore hardness in the range of 2A to 25A.

15. The vaginal barrier device method of claim 11, said single unit of flexible material further comprising a silicone rubber proven to be safe for prolonged contact with skin, in conformance with standards ISO 10993-10 and OECD TG 439.

16. The vaginal barrier device method of claim 11, said single unit of flexible material further comprising a silicone rubber allowing casting in a mold in one piece.

17. The vaginal barrier device method of claim 11, said single unit of flexible material further comprising a silicone rubber that does not leech out any substance or absorb any substance after curing, in use.

18. The vaginal barrier device method of claim 11, said single unit of flexible material further comprising a silicone rubber capable of withstanding high heat and harsh chemicals used for cleaning and sterilization.

19. The vaginal barrier device method of claim 11, said vaginal barrier device further having dimensions in the ranges of 6 cm-7 cm in length of said flexible stem, 0.5 cm-1cm in diameter of said flexible stem, 2 cm-4 cm in diameter of said first circular barrier and said intermediate circular barriers, 1cm-2 cm increments of spacing between said circular barriers, and 2 mm-4 mm in thickness of said circular barriers at said flexible stem, tapering down towards the circumference.

20. An apparatus comprising:
a unitary flexible body sized for positioning in a vaginal opening without contacting a cervix, the unitary flexible body further shaped to seal off the vaginal opening to resist entry of fluid through the vaginal opening and into a vaginal canal, the flexible body comprising:
a flexible stem of substantially uniform linear and non-hollow cylindrical form, having a long axis between an upward end and a downward end and a substantially uniform cross-sectional geometry along a length of the flexible stem which extends into the vaginal canal in an inserted position;
an end grip at the downward end of said flexible stem, said end grip resting at the vaginal opening when said vaginal barrier device is in the inserted position;
a first circular barrier at the upward end of said flexible stem, wherein the first circular barrier is flexible and comprises an upwardly facing outwardly convex central portion and a bendable disk-shaped sealing portion unitarily connected to, and extending outwardly from, the central portion; and
at least three intermediate circular barriers arrayed in a spaced-apart relationship along said flexible stem, each of the at least three intermediate circular barriers being independently flexible to be deflected in a concave manner and deflected in a convex manner along the long axis of the flexible stem;

wherein the first circular barrier and the at least three intermediate circular barriers are arrayed co-axially along the flexible stem, extending, at rest, substantially perpendicularly radially outward from the flexible stem, the first circular barrier and the at least three intermediate circular barriers each comprising a periphery defining a resting circumference co-axial with the flexible stem;

wherein the first circular barrier and the at least three intermediate circular barriers have a tapering profile from a relative thickness portion proximate the flexible stem to a relative thinness portion at the periphery of each of the first circular barrier and the at least three intermediate circular barriers; and wherein, when the device is positioned, the thickness portions of the first circular barrier and each said intermediate circular barrier provides a force tending to restore the circular barrier to its resting position which urges the thinness portions of the first circular barrier and each said intermediate circular barrier against a vaginal wall to seal off the vaginal opening and prevent entry of fluids into the vaginal canal from an exterior of a woman's body; said vaginal barrier device is capable of being used to seal the vagina against intrusion of fluid from the exterior of the woman's body and prevent, entry of potentially contaminated fluid during immersion activities.

* * * * *